(12) United States Patent
Appleman et al.

(10) Patent No.: US 9,161,946 B2
(45) Date of Patent: Oct. 20, 2015

(54) DOSING METHODS FOR TREATING DISEASE

(71) Applicant: Anadys Pharmaceuticals, Inc., San Diego, CA (US)

(72) Inventors: James Appleman, San Diego, CA (US); Joyce Tan, San Diego, CA (US); Simon Fletcher, San Diego, CA (US)

(73) Assignee: Anadys Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 14/101,449

(22) Filed: Dec. 10, 2013

(65) Prior Publication Data

US 2014/0094427 A1    Apr. 3, 2014

Related U.S. Application Data

(63) Continuation of application No. 12/674,136, filed as application No. PCT/US2008/073594 on Aug. 19, 2008, now abandoned.

(60) Provisional application No. 61/078,432, filed on Jul. 6, 2008, provisional application No. 60/979,189, filed on Oct. 11, 2007, provisional application No. 60/956,859, filed on Aug. 20, 2007.

(51) Int. Cl.
| | | |
|---|---|---|
| *A01N 43/04* | (2006.01) | |
| *A61K 31/70* | (2006.01) | |
| *A61K 31/7064* | (2006.01) | |
| *A61K 31/40* | (2006.01) | |

(52) U.S. Cl.
CPC ............. *A61K 31/7064* (2013.01); *A61K 31/40* (2013.01)

(58) Field of Classification Search
CPC .......................... A61K 31/7064; A61K 31/40
See application file for complete search history.

(56) References Cited

U.S. PATENT DOCUMENTS

| 6,362,166 | B1 * | 3/2002 | Webber et al. ................. 514/1.3 |
| 6,667,299 | B1 * | 12/2003 | Ahlem et al. .................. 514/178 |
| 6,924,271 | B2 * | 8/2005 | Averett et al. ................... 514/43 |
| 7,321,033 | B2 * | 1/2008 | Averett et al. ................ 536/27.2 |
| 7,528,115 | B2 * | 5/2009 | Haley et al. ...................... 514/43 |
| 7,557,190 | B2 * | 7/2009 | Barbosa et al. ............. 530/387.1 |
| 7,560,544 | B2 | 7/2009 | Webber et al. |
| 7,576,068 | B2 * | 8/2009 | Averett ........................... 514/45 |
| 7,709,448 | B2 | 5/2010 | Haley et al. |
| 7,745,415 | B2 * | 6/2010 | Averett et al. .................... 514/42 |
| 7,928,085 | B2 | 4/2011 | Kucera et al. |
| 7,943,759 | B2 * | 5/2011 | Averett et al. ................ 536/27.2 |
| 8,097,718 | B2 * | 1/2012 | Webber et al. ............... 536/27.2 |
| 8,883,758 | B2 * | 11/2014 | Webber et al. .................. 514/46 |
| 2005/0054590 | A1 | 3/2005 | Averett |
| 2005/0256095 | A1 | 11/2005 | Ahlem et al. |
| 2006/0160830 | A1 | 7/2006 | Webber et al. |
| 2007/0161783 | A1 | 7/2007 | Barbosa et al. |

FOREIGN PATENT DOCUMENTS

| EP | 0343945 A2 | 11/1989 |
| WO | WO-9817279 A1 | 4/1998 |
| WO | WO-9951608 A1 | 10/1999 |

OTHER PUBLICATIONS

International Search Report and Written Opinion, International Application No. PCT/US08/73594 dated Dec. 18, 2008.

* cited by examiner

*Primary Examiner* — Lawrence E Crane
(74) *Attorney, Agent, or Firm* — Womble Carlyle Sandridge & Rice LLC (57) ABSTRACT

The invention relates to a method for treating disease such as viral infections, tumors, and cancers, comprising administering a TLR7 agonist or TLR7 agonist prodrug according to a cyclical dosing schedule having a dosing period and a resting period. For example, the method encompasses treating disease with:

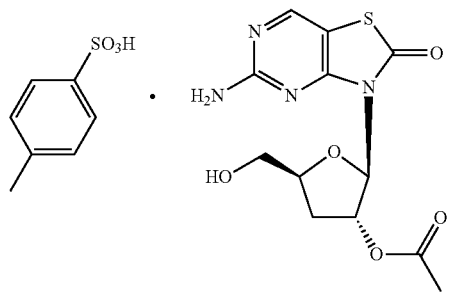

5-amino-3-(2'-O-acetyl-3'-deoxy-β-D-ribofuranosyl)-3H-thiazolo[4,5-d]pyrimidin-2-one Tosylate
according to a dosing schedule of every-other-day or a dosing schedule of three consecutive days of dosing followed by four consecutive days of not dosing.

4 Claims, 6 Drawing Sheets

* B cell expression of Ki67 on day 1 was not measured in this study.

DOSING METHODS FOR TREATING DISEASE

CROSS-REFERENCE TO RELATED APPLICATIONS

The present application is a continuation of U.S. application Ser. No. 12/674,136 filed Mar. 25, 2011, which is a national stage application of PCT/US08/73594 filed Aug. 19, 2008, which claims the benefit of U.S. Application No. 61/078,432 filed Jul. 6, 2008, U.S. Application No. 60/979,189 filed Oct. 11, 2007 and U.S. Application No. 60/956,859 filed Aug. 20, 2007, the disclosures of which are incorporated herein by reference.

FIELD OF THE INVENTION

The invention relates to cyclic dosing schedules comprising dosing a therapeutically effective amount of a Toll-like receptor 7 ("TLR7") agonist or a TLR7 agonist prodrug for at least one day followed by a resting period wherein the TLR7 agonist or the TLR7 agonist prodrug is not dosed for at least one day. For instance, the invention encompasses dosing 5-amino-3-(2'-O-acetyl-3'-deoxy-beta-D-ribofuranosyl)-3H-thiazolo[4,5-d]pyrimidin-2-one, or a pharmaceutically acceptable salt thereof, according to a cyclic dosing schedule.

BACKGROUND

Pharmacological enhancement of immune responses for the treatment of disease, particularly viral and bacterial infections and cancer, is attractive for several reasons. Beyond the obvious observation that the immune system is generally responsible for clearing pathogens, the breadth of an immune response offers the potential to react to infectious disease with a low risk of developing drug resistance. Also, immune-based therapy offers the potential to address the treatment of infections where direct replication inhibitors are either absent or unsatisfactory. Some viruses offer only poor prospects for development of effective agents directed at virally encoded targets due to their replication strategies, while others are so genetically plastic that the inhibitory effect of a direct replication inhibitor is lost rapidly, unless effective strategies are taken to suppress the evolution of resistant variants.

Several clinical observations support the importance of tumor immune surveillance in humans. The increased risk of tumor development in immunosuppressed patients, cases of spontaneous tumor regression, and the presence of tumor-reactive T cells and B cells correlating with improved prognosis all point to a role for the immune system in controlling tumor growth. Studies comparing histopathology with clinical outcome for early-stage lesions in several cancer types have demonstrated that intratumoral lymphocyte infiltrates are strongly correlated with reduced frequencies of metastasis (Taylor et al. J. CLIN. ONC. 25(7):869-75 (2007)) and improved patient survival (Sharma et al. PNAS 104(10):3967-72 (2007)). It is clear that the balance between stimulation and suppression of the host immune response plays an essential role in the ability of cancer cells to grow, invade, and metastasize. Recognition and elimination of these malignant cells is a major challenge for the host immune system. Two reasons that immune control of tumor growth is inadequate are that tumors are capable of locally suppressing host immunity and many tumors are intrinsically poorly immunogenic. Immunotherapy has had some success in treating selected tumors and the potential to harness the immune system as a therapeutic modality remains of great interest to many oncologists. First generation immunotherapies were single cytokines, such as Interferon-α (IFN-α) for the treatment of melanoma and renal cell carcinoma (Moschos et al. CANCER TREAT. RES. 126:207-41 (2005)). With this approach, the number of patients who responded to therapy was small, but for those who did, the response could be profound and sometimes curative.

The advent of molecular biology has enabled products based on interferon ("IFN"), an immune cytokine, which is a component in the treatment of hepatitis C virus ("HCV") infection and in the treatment of some tumors. The biological importance of IFN in antiviral host defense and in cancer therapy has spawned many efforts to identify agents that stimulate endogenous IFN production. Stimulation of IFN production has been reported with agonists of Toll-like receptors ("TLRs"), which has accelerated efforts to exploit them for therapeutic benefit. TLRs are a family of pathogen-recognition receptors that when activated by appropriate agonists (e.g., LPS, viral double-stranded RNA, flagellin, etc.) activate the innate immune response (Iwasaki and Medzhitov, NAT. IMMUNOL. 5(10):987-95 (2004)). Stimulation of TLRs either directly or indirectly leads to: (i) the release of multiple cytokines, including type I and type II interferons; (ii) the induction of pathways and enzymes that destroy intracellular pathogens; and (iii) the maturation of professional antigen-presenting cells, resulting in the activation of the innate and adaptive immune response. The benefit of many of these responses in the treatment of viral diseases and cancers, notably stimulation of type I and type II interferons and NK and T cell activation, is well-recognized. To date, 10 functional TLRs have been identified in humans.

In general, drugs are administered as immediate-release dosage forms so that the entire dose of the drug is released within a very short period of time following administration. As the bolus of released drug is absorbed, the plasma drug concentration rapidly rises to a maximal or peak concentration and subsequently declines as the drug undergoes "clearance". During some portion of the time period in which the plasma drug concentration rises, peaks and subsequently declines, the drug provides its therapeutic effects, i.e., the plasma drug concentration achieves or exceeds a therapeutically effective concentration for the disease or condition being treated. Likewise, the therapeutic effect disappears when the plasma drug concentration and physiological response thereto declines to a level that is below a certain threshold. These principals hold true not only for drugs administered orally but also for drugs administered by intravenous bolus and for many small molecules when administered by subcutaneous injection.

In certain instances, drugs are delivered in slow-release form, in an attempt to sustain plasma drug levels so as to sustain the duration of benefits. In these cases, the duration of benefit again tracks with the duration of drug exposure. In other instances, typically with agonists that activate rather than inhibit their respective targets, benefit persists beyond the duration of drug exposure. For example, activation of a host receptor can lead to activation of cellular responses, the benefit of which can persist beyond the period of time in which the receptor is activated by circulating drug levels.

In all the cases cited above, immediate release, sustained release and agonists with a durable period of action, it is expected that the magnitude of beneficial effects correlates with the amount of drug administered, i.e. more administered drug leads to more benefit.

For drugs administered in this fashion, relatively high peaks and low valleys of plasma concentrations cannot be avoided. Accordingly, doses and dosing intervals can be selected to help obtain an acceptable balance between average steady-state plasma drug concentrations that provide effective therapy and avoiding, as much as possible, problematical peak and/or trough plasma concentrations during each dosing interval. Typically the minimal acceptable dosing frequency for a particular drug is set by constraints imposed by toxicity and efficacy. Dosing too often results in toxicity, and dosing too infrequently is inefficacious. For example, the response in genotype 1 infected HCV patients to administration of IFN-α in combination with ribavirin demonstrates that benefit increases with duration of exposure during a standard treatment interval. Specifically, daily dosing of standard interferons induces a substantially more rapid initial decline in viral load than does three times weekly ("TIW") administration of the same agent (deLedinghen et al., J. HEPATOL., 36(6):819-26 (2002); Perez et al., J. VIRAL HEPAT., 10(6):437-45 (2003)). Furthermore, sustained viral response increases with use of sustained exposure interferon (e.g. pegylated interferon) when compared to TIW administration of standard interferons, which are cleared relatively rapidly (33-36% for standard interferons to 42-46% for sustained exposure interferons (Maims et al., NAT. REV. DRUG DISCOV., 6(12): 991-1000 (2007)). Surprisingly, while daily dosing or continuous exposure is optimal for IFN-α, it is suboptimal for TLR7 agonists generally, TLR7 agonists and TLR7 agonist prodrugs and the treatment of viral infection in particular.

SUMMARY OF THE INVENTION

Figure 1:
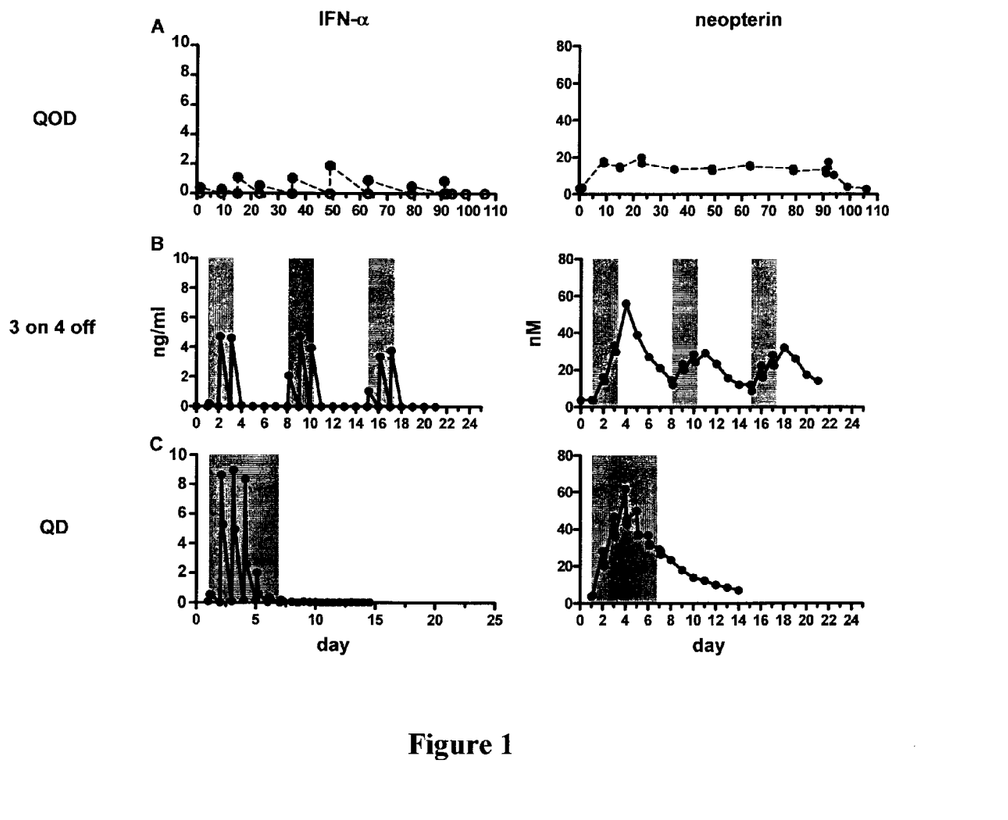
FIG. 1 shows interferon-α and neopterin responses to 100 mg/kg Compound I as the tosylate according to (A) an every-other-day dosing schedule (QOD), (B) a dosing schedule of 3 consecutive days of dosing followed by 4 consecutive days of resting ('3 on 4 off'), and (C) a daily (QD) dosing schedule for 7 consecutive days of dosing with 7 days of follow-up. For panels B and C, the gray backgrounds indicate dosing days.
Figure 2:
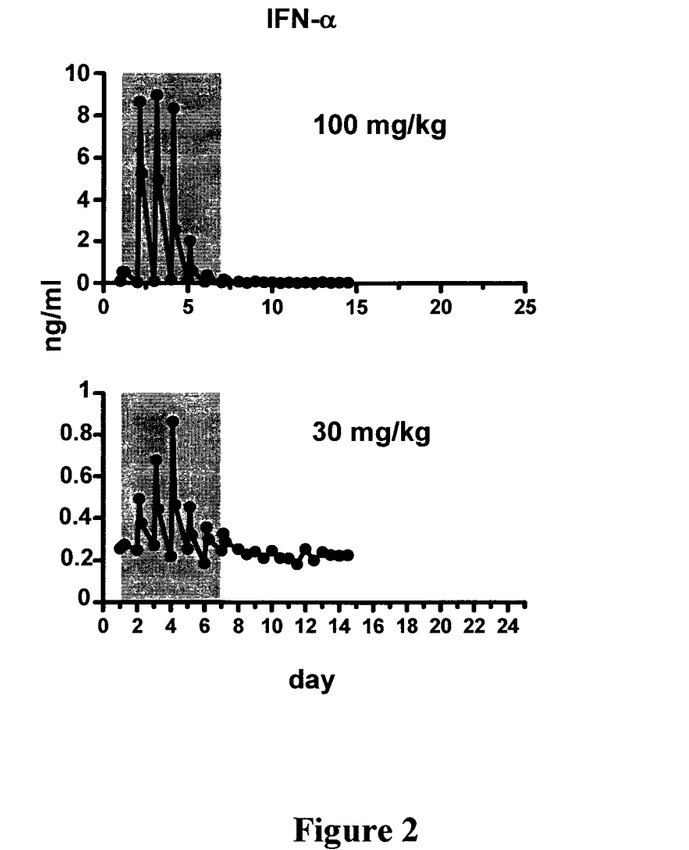
FIG. 2 compares the interferon-α response at different dosing concentrations (30 mg/kg and 100 mg/kg) of Compound I as the tosylate according to a daily dosing (QD) schedule for 7 consecutive days with 7 days of follow-up. The gray backgrounds indicate dosing days.

The invention relates to cyclical dosing methods of TLR7 agonists and TLR7 agonist prodrugs for the treatment of disease. Although daily dosing initially elicits strong cytokine stimulation that temporarily escalates upon repeated dosing, the inventors discovered that this response is unexpectedly down-modulated after only 3-4 days (FIG. 1C). It was discovered that this down-modulation is dependent on dose schedule and not upon the magnitude of response, since down-modulation is also triggered after administration of lower concentrations of the TLR7 agonist (FIG. 2). The inventors found that the unexpected drop-off in immune response is avoided when certain cyclic dosing schedules are employed.

Contrary to the teachings in the art, not only do the disclosed cyclic dosing schedules prevent a drop-off in immune response, but they instead reproducibly induce a state of immune activation appropriate for therapeutic use. The cyclical dosing schedules described herein provide immune induction that is qualitatively and reasonably quantitatively repeatable from cycle to cycle, while inducing a therapeutically effective level of immune activation that is well tolerated with an avoidance of adverse toxicology findings. It is surprising that the cyclic dosing schedules achieve a greater presumptive efficacy at a lower dose as compared to daily dosing.

TLR7 agonists and TLR7 agonist prodrugs are known in the art. In one aspect of the invention, the TLR7 agonist or TLR7 agonist prodrug may be a 3,5-disubstituted-3H-thiazolo[4,5-d]pyrimidin-2-one such as 5-amino-3-(2'-O-acetyl-3'-deoxy-beta-D-ribofuranosyl)-3H-thiazolo[4,5-d]pyrimidin-2-one (hereafter referred to as "Compound I"), which is depicted below.

Compound I

Compound I may be in the form of a pharmaceutically acceptable salt such as the tosylate salt depicted below (hereafter referred to as "Compound I Tosylate").

Compound I

Tosylate

In one aspect, the invention comprises a method for administering a TLR7 agonist or TLR7 agonist prodrug according to a cyclical dosing schedule. The dosing schedule results in less down-regulation of cytokines and chemokines and correspondingly greater anticipated efficacy than a continuous once-a-day administration of the TLR7 agonist or TLR7 agonist prodrug. In one embodiment, the TLR7 agonist or TLR7 agonist prodrug is not bropirimine.

In another aspect, the invention comprises a method of reducing down-modulation of cytokine or neopterin induction comprising administering a TLR7 agonist or TLR7 agonist prodrug to a patient in need thereof according to a cyclical dosing schedule, wherein a cycle comprises a dosing period of at least one day in which a therapeutically effective amount of the TLR7 agonist or TLR7 agonist prodrug is administered, followed by a resting period of at least one day in which the TLR7 agonist or TLR7 agonist prodrug is not administered. In another embodiment, the amount of down-modulation of cytokine stimulation during a cycle is less than the amount of down-modulation of immune stimulation for the same TLR7 agonist or TLR7 agonist prodrug when administered according to a once-a-day dosing schedule.

In one aspect, the dosing period is independently selected from 1, 2, 3, 4, and 5 days and the TLR7 agonist or TLR7 agonist prodrug is administered every day during the dosing period, and the resting period is independently selected from 1, 2, 3, 4, and 5 days. For instance, the dosing period may be 3-4 consecutive days and the resting period may be 3-4 consecutive days. Additionally, the dosing period may be 3 consecutive days and the resting period may be 4 consecutive days. Moreover, the dosing period may be 1 day and the resting period may be 1 day, i.e., an every-other-day dosing schedule. The dosing schedule can be maintained, for example, for at least 2, 3, 4, or 5 cycles, and longer (e.g., 200 cycles) or indefinitely.

In another aspect, the invention comprises a method for treating disease according to the dosing schedules described above. Diseases encompassed include, for example, asthma and allergy, viral infections, tumors, and cancers. For instance, the viral infection may be selected from an RNA or DNA virus including adenovirus, cytomegalovirus, hepatitis A virus (HAV), hepadnaviruses including hepatitis B virus (HBV), flaviviruses including Yellow Fever virus, hepaciviruses including hepatitis C virus (HCV), herpes simplex type 1 and 2, herpes zoster, human herpesvirus 6, human immunodeficiency virus (HIV), human papilloma virus (HPV), influenza A virus, influenza B virus, measles, parainfluenza virus, pestivirus, poliovirus, poxvirus, rhinovirus, coronovirus, respiratory syncytial virus (RSV), multiple families of viruses that cause hemorrhagic fevers, including the Arenaviruses, the Bunyaviruses and Filoviruses, and a range of viral encephalitides caused by RNA and DNA viruses. In particular, one or both of the described dosing schedules are effective in treating HCV infection.

Examples of cancers and tumors envisioned by the instant disclosure encompass, but are not limited to those caused by a virus, and the effect may involve inhibiting the transformation of virus-infected cells to a neoplastic state, inhibiting the spread of viruses from transformed cells to other normal cells, and/or arresting the growth of virus-transformed cells. The dosing schedules described herein are expected to be useful against a broad spectrum of tumors including but not limited to carcinomas, sarcomas, and leukemias. Included in such a class are mammary, colon, bladder, lung, prostate, stomach, and pancreas carcinomas and lymphoblastic and myeloid leukemia.

In certain embodiments, the above dosing schedules comprise a dosing period wherein a daily dose of from about 0.01 mg/kg to about 100 mg/kg of the TLR7 agonist or TLR7 agonist prodrug is administered to a patient. For example, the patient may be a human. In another embodiment, the above methods comprise a dosing period wherein the daily dose is from about 0.1 mg/day to about 10,000 mg/day.

The features of the present invention along with the attendant advantages thereof will be more fully appreciated upon a reading of the following detailed description in combination with the examples and accompanying figures.

DETAILED DESCRIPTION

The term "comprising" (and its grammatical variations) as used herein is in the inclusive sense of "having" and "including" and not in the exclusive sense of "consisting only of". The terms "a" and "the" as used herein are understood to encompass the plural as well as the singular.

The term "preventing" refers to the ability of a compound or composition of the invention to prevent a disease identified herein in patients diagnosed as having the disease or who are at risk of developing such disease. The term also encompasses preventing further progression of the disease in patients who are already suffering from or have symptoms of such disease.

The term "patient" or "subject" means an animal (e.g., cow, horse, sheep, pig, chicken, turkey, quail, cat, dog, mouse, rat, rabbit, guinea pig, etc.) or a mammal, including chimeric and transgenic animals and mammals. In the treatment or prevention of disease, the term "patient" or "subject" preferably means a monkey or a human, most preferably a human.

The term a "therapeutically effective amount" refers to an amount of the compound of the invention sufficient to provide a benefit in the treatment or prevention of disease. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with other therapeutic agents.

The term "treating" refers to:
(i) preventing a disease, disorder, or condition from occurring in an animal that may be predisposed to the disease, disorder and/or condition, but has not yet been diagnosed as having it;
(ii) inhibiting the disease, disorder, or condition, i.e., arresting its development; and
(iii) relieving the disease, disorder, or condition, i.e., causing regression of the disease, disorder, and/or condition.

The phrase "reducing down-modulation of immune stimulation" or "reducing down-modulation of a cytokine stimulation" refers to reducing the amount of down-modulation of immune stimulation or cytokine stimulation with a cyclical dosing schedule wherein the amount of down-modulation is reduced relative to the amount of down-modulation observed when Compound I is administered daily over a period of time. For instance, the amount of reduction can be at least 5%, 10%, 25%, or 50%, or equal to 100% and the period of time may be at least 7 days, 14 days, 28 days, and longer.

The terms "α" and "β" indicate the specific stereochemical configuration of a substituent at an asymmetric carbon atom in a chemical structure as drawn.

The terms "pharmaceutically acceptable acid addition salt" or "pharmaceutically acceptable salt", which are used interchangeably herein, are meant those salts in which the anion does not contribute significantly to the toxicity or pharmacological activity of the salt, and, as such, they are substantially the pharmacological equivalent of the TLR7 agonist or TLR7 agonist prodrug. Examples of pharmaceutically acceptable acids that are useful for the purposes of salt formation include but are not limited to hydrochloric, hydrobromic, hydroiodic, sulfuric, citric, tartaric, methanesulfonic, fumaric, malic, maleic and mandelic, and others. One preferred pharmaceutically acceptable acid addition salt is the p-toluene sulfonic acid salt of Compound I.

The term "dosage form" is meant a pharmaceutical composition or device comprising an active pharmaceutical agent, such as a TLR7 agonist or TLR7 agonist prodrug, the composition or device optionally containing inactive ingredients, i.e., pharmaceutically acceptable excipients such as suspending agents, surfactants, disintegrants, binders, diluents, lubricants, stabilizers, antioxidants, osmotic agents, colorants, plasticizers, coatings and the like, that are used to manufacture and deliver active pharmaceutical agents.

The term "immediate-release dosage form" refers to a dosage form that releases drug substantially completely within a short time period following administration, i.e., generally within a few minutes to about 1 hour.

TLR7 agonists and TLR7 agonist prodrugs are known in the art. For examples, a variety of TLR7 agonists and TLR7 agonist prodrugs are described in U.S. Patent Application Publication No. 2005/0054590 (application Ser. No. 10/931,130) and U.S. Patent Application Publication No. 2006/0160830 (application Ser. No. 11/304,691), which are both incorporated herein by reference in their entirety. For instance, the TLR7 agonist or TLR7 agonist prodrug may be Compound I (3,5-disubstituted-3H-thiazolo[4,5-d]pyrimidin-2-one such as 5-amino-3-(2'-O-acetyl-3'-deoxy-beta-D-ribofuranosyl)-3H-thiazolo[4,5-d]pyrimidin-2-one), which is depicted below.

Compound I

The above compound has three asymmetric carbons and may be utilized as the racemate (i.e., a non-optically active form of the drug), as a single diastereomer or enantiomer or as mixtures thereof. The free base form of Compound I, in accordance with general pharmaceutical practice, is typically formulated as a pharmaceutically acceptable salt for inclusion in an oral dosage form. Accordingly, the term, "Compound I" unless otherwise indicated, refers to both the free base form and to a pharmaceutically acceptable salt form of the drug, and includes the non-optically-active and optically active forms of the drug, either individually or as mixtures.

Compound I may be in the form of a pharmaceutically acceptable salt such as the tosylate salt depicted below.

Tosylate

Certain acid addition salts of 3,5-disubstituted-3H-thiazolo[4,5-d]pyrimidin-2-one compounds and their preparation are described in U.S. Application Publication No. 2006/0160830 (application Ser. No. 11/304,691, which is incorporated herein by reference in its entirety. In particular, this application describes the synthesis of Compound I (5-Amino-3-(2'-O-Acetyl-3'-Deoxy-β-D-Ribofuranosyl)-3H-Thiazole[4,5-d]pyrimidine-2-one), and in particular the P-toluene sulfonic acid salt of Compound I.

In one aspect, the invention comprises a method for administering a TLR7 agonist or TLR7 agonist prodrug according to a cyclical dosing schedule, wherein each cycle comprises dosing for a predetermined number of days followed by a resting period of a predetermined number of days. The dosing schedule results in less down-regulation of cytokines and/or immune response and correspondingly greater anticipated benefit than a continuous once-a-day administration of the TLR7 agonist or TLR7 agonist prodrug. In one embodiment, the TLR7 agonist or TLR7 agonist prodrug is not bropirimine.

In another aspect, the invention comprises a method of reducing down-modulation of cytokine or neopterin induction comprising administering a TLR7 agonist or TLR7 agonist prodrug to a patient in need thereof according to a cyclical dosing schedule, wherein a cycle comprises a dosing period of at least one day in which a therapeutically effective amount of the TLR7 agonist or TLR7 agonist prodrug is administered, followed by a resting period of at least one day in which the TLR7 agonist or TLR7 agonist prodrug is not administered. In one embodiment, the amount of down-modulation of cytokine stimulation during a dosing period of a cycle is less than the amount of down-modulation of immune stimulation for the same TLR7 agonist or TLR7 agonist prodrug when administered according to a once-a-day dosing schedule.

In one aspect, the dosing period is independently selected from 1, 2, 3, 4, and 5 days and the TLR7 agonist or TLR7 agonist prodrug is administered once daily, and the resting period is independently selected from 1, 2, 3, 4, and 5 days. For instance, the dosing period may be 3-4 consecutive days and the resting period may be 3-4 consecutive days. Additionally, the dosing period may be 3 consecutive days and the resting period may be 4 consecutive days. Moreover, the dosing period may be 1 day and the resting period may be 1 day, i.e., an every-other-day dosing schedule. The dosing schedule can be maintained, for example, for at least 2, 3, 4, or 5 cycles, and longer (e.g., 200 cycles) or indefinitely.

In another aspect, the invention comprises a method for treating disease according to the dosing schedules described above. Diseases encompassed include, for example, asthma and allergy, viral infections, tumors, and cancers. For instance, the viral infection may be selected from an RNA or DNA virus including adenovirus, cytomegalovirus, hepatitis A virus (HAV), hepadnaviruses including hepatitis B virus (HBV), flaviviruses including Yellow Fever virus, hepaciviruses including hepatitis C virus (HCV), herpes simplex type 1 and 2, herpes zoster, human herpesvirus 6, human immunodeficiency virus (HIV), human papilloma virus (HPV), influenza A virus, influenza B virus, measles, parainfluenza virus, pestivirus, poliovirus, poxvirus, rhinovirus, coronovirus, respiratory syncytial virus (RSV), multiple families of viruses that cause hemorrhagic fevers, including the Arenaviruses, the Bunyaviruses and Filoviruses, and a range of viral encephalitides caused by RNA and DNA viruses. In particular, the described dosing schedules are effective in treating HCV infection.

Examples of cancers and tumors envisioned by the instant disclosure encompass, but are not limited to those caused by a virus, and the effect may involve inhibiting the transformation of virus-infected cells to a neoplastic state, inhibiting the spread of viruses from transformed cells to other normal cells, and/or arresting the growth of virus-transformed cells. The dosing schedules described herein are expected to be useful against a broad spectrum of tumors including, but not limited to carcinomas, sarcomas, and leukemias. Included in such a class are mammary, colon, bladder, lung, prostate, stomach, and pancreas carcinomas and lymphoblastic and myeloid leukemia.

Another aspect of the invention provides methods of preventing or treating infections of a warm-blooded animal, especially a human, by a pathogenic organism such as the bacterial, fungal or viral infections disclosed in WO2005/121162 (which is incorporated herein by reference in its entirety). In one embodiment, the viral infection is cytomegalovirus, hepatitis A virus (HAV), hepatitis B virus (HBV), flaviviruses including Yellow Fever virus and hepatitis C virus (HCV), herpes simplex type 1 and 2, herpes zoster, human herpesvirus 6, human immunodeficiency virus (HIV), human papilloma virus (HPV), influenza A virus, influenza B virus, measles, parainfluenza virus, poliovirus, poxvirus (including smallpox and monkeypod virus), rhinovirus, respiratory syncytial virus (RSV), multiple families of viruses that cause hemorrhagic fevers, including the Arenaviruses (LCM, Junin virus, Machup virus, Guanarito virus, and Lassa Fever), the Bunyaviruses (Hanta viruses and Rift Valley Fever) and Filoviruses (Ebola and Marburg virus), a range of viral encephalitides including West Nile virus, LaCrosse virus, California Encephalitis virus, Venezuelan Equine Encephalitis virus, Eastern Equine Encephalitis virus, Western Equine Encephalitis virus, Japanese Encephalitis virus, Kysanur Forest virus, or tickborne viruses such as Crimean-Congo Hemorrhagic fever virus. In another embodiment, the virus is hepatitis B virus or hepatitis C virus.

In certain embodiments, the above dosing schedules comprise a dosing period wherein a daily dose of from about 0.01 mg/kg to about 100 mg/kg of the TLR7 agonist or TLR7 agonist prodrug is administered to a patient. For example, the patient may be a human. In another embodiment, the above methods comprise a dosing period wherein the daily dose is from about 0.1 mg/day to about 10,000 mg/day.

Although Compound I Tosylate has been exemplified herein, other pharmaceutically acceptable acid addition salts are well-known to those of ordinary skill in the art. Non-limiting examples of pharmaceutically acceptable acid addition salts include hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts.

To elucidate the effects of dosing on immune activation, a number of pharmacology studies were performed in cynomolgus monkeys with Compound I tosylate, which are presented below. The amount of Compound I administered as the tosylate salt reported therein refers to the amount of Compound I administered and does not include the contribution of the tosylate to the total amount of the dose.

EXAMPLES

The pharmacodynamic response of a continuous daily dosing schedule (QD) was compared to a cyclic dosing schedule of every-other-day (QOD) and a cyclic dosing schedule of 3 consecutive days of dosing followed by 4 consecutive days of resting ('3 on 4 off'). All three dosing schedules were conducted with orally administered Compound I Tosylate. Immune parameters measured include cytokine and chemokine secretion in plasma measured by multiplexed immunoassay, neopterin levels in plasma measured by Enzyme Linked Immunosorbant Assay (ELISA), and cytotoxic T cell (CD8 T) effector proliferative state and B cell proliferative state in peripheral blood leukocytes as measured by flow cytometry analysis of Ki67 levels.

Example 1

Every-Other-Day Dosing Schedule (QOD)

Cynomolgus macaques were given 10, 30, 100 or 300 mg/kg (Compound I equivalents) of Compound I Tosylate according to an every-other-day dosing schedule for 14 days, 28 days, or 13 weeks followed by recovery periods of various lengths. The immune response was determined by measuring cytokine and neopterin levels in plasma, as well as B cell and T cell responses in peripheral blood.

Figure 3:
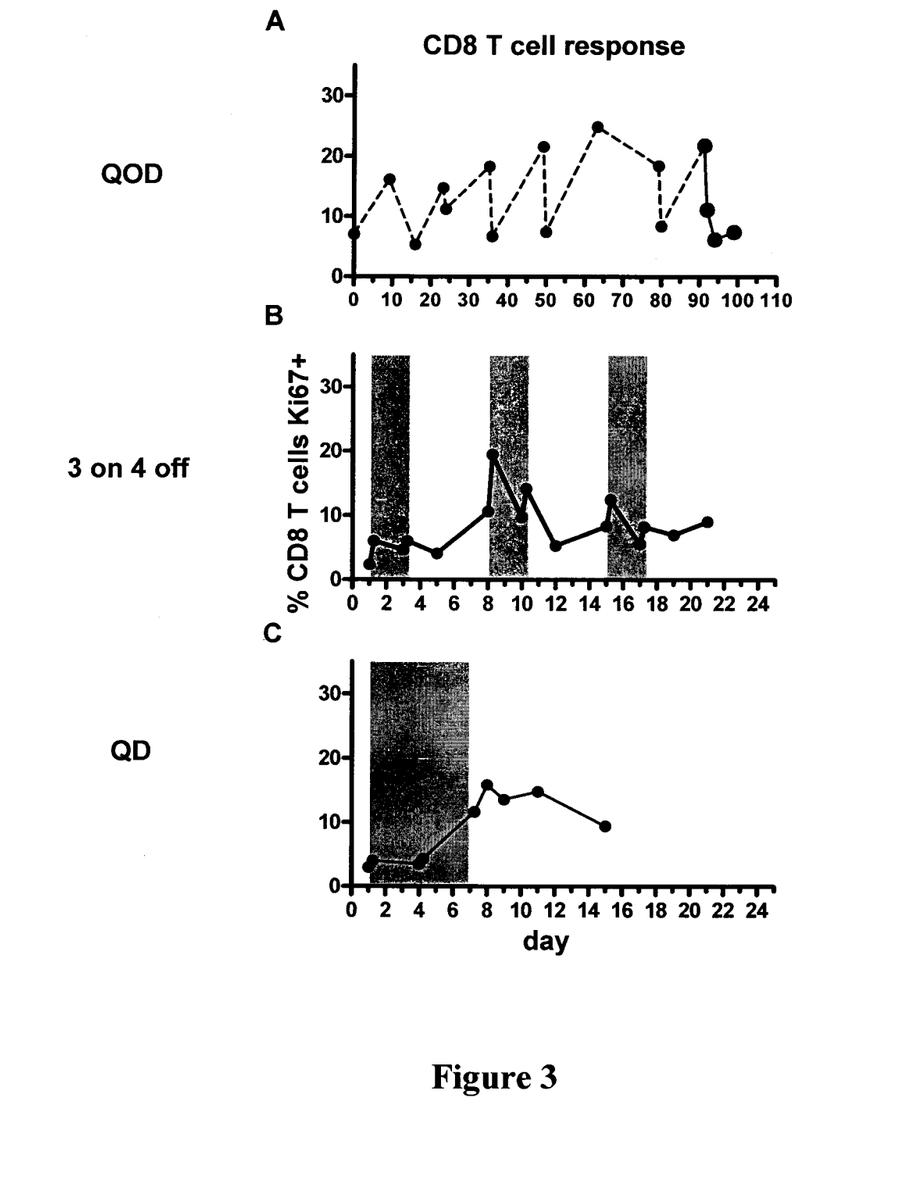
FIG. 3 shows the cytotoxic T cell (CD8 T) effector proliferative state to 100 mg/kg Compound I as the tosylate according to (A) an every-other-day dosing schedule (QOD), (B) a dosing schedule of 3 consecutive days of dosing followed by 4 consecutive days of resting ('3 on 4 off'), and (C) a daily dosing (QD) schedule for 7 consecutive days with 7 days of follow-up. For panels B and C, the gray backgrounds indicate dosing days.
Figure 4:
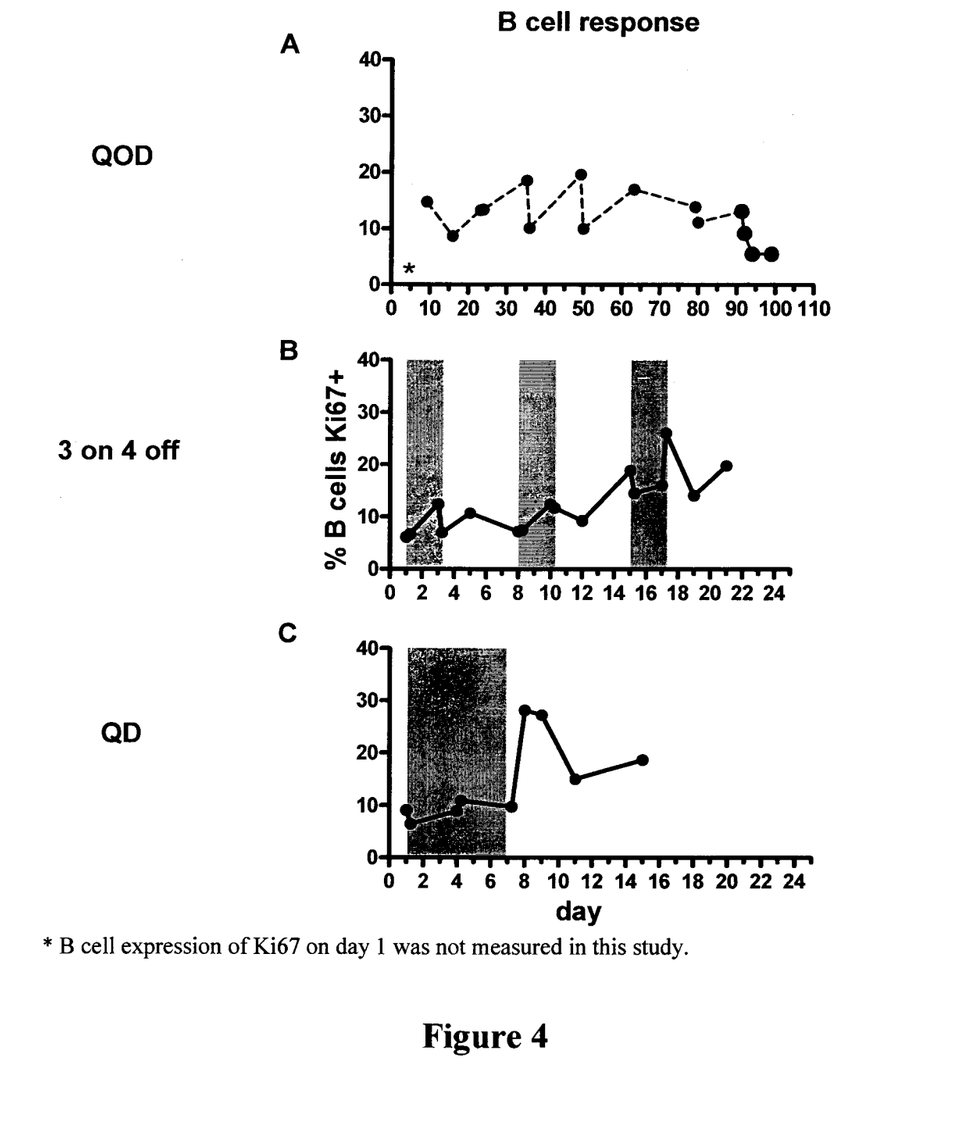
FIG. 4 shows the induction of B cell proliferative state in response to 100 mg/kg Compound I as the tosylate according to (A) an every-other-day dosing schedule (QOD), (B) a dosing schedule of 3 consecutive days of dosing followed by 4 consecutive days of resting ('3 on 4 off'), and (C) a daily dosing (QD) schedule for 7 consecutive days with 7 days of follow-up. For panels B and C, the gray backgrounds indicate dosing days.

The every-other-day dosing schedule repeatedly induced moderate levels of cytokine, chemokine, neopterin and cellular responses that, for the most part, did not build with repeated doses as shown for IFN-α, neopterin and cellular responses in FIGS. 1A, 3A, and 4A. IFN-α levels were repeatedly induced to a reasonably comparable magnitude with this schedule (Table 1), as discussed below, although the average peak levels of IFN-α induced were less than those elicited by 7 consecutive days of dosing. Similarly, IP-10, a marker of responsiveness to IFN-α, was reproducibly induced by this regimen, as were B- and T-cell responses. The magnitude of the B cell response is reduced with this schedule compared to other dose schedules (FIG. 4). Neopterin levels were induced and sustained during the entire dosing period with this alternate day regimen (FIG. 1A). The cytokine and cellular responses declined significantly 24 hours after the last dose.

The every-other-day (QOD) schedule produced the most stable immune enhancement and minimized reduction in down-modulation of the cytokine and chemokine and accompanying neopterin responses across the various dosing schedules investigated. Surprisingly, an every-other-day dosing schedule showed a sustained effect of cytokine induction over repeated dosing cycles despite about a 3-10 fold reduction in absolute magnitude of peak cytokine levels induced (compared to the peak with once daily dosing) when the daily dose is 100 mg/kg for both schedules (QOD vs. QD). Importantly, the neopterin response was induced and maintained at both the 30 mg/kg and 100 mg/kg dose groups with QOD dosing.

Figure 6:
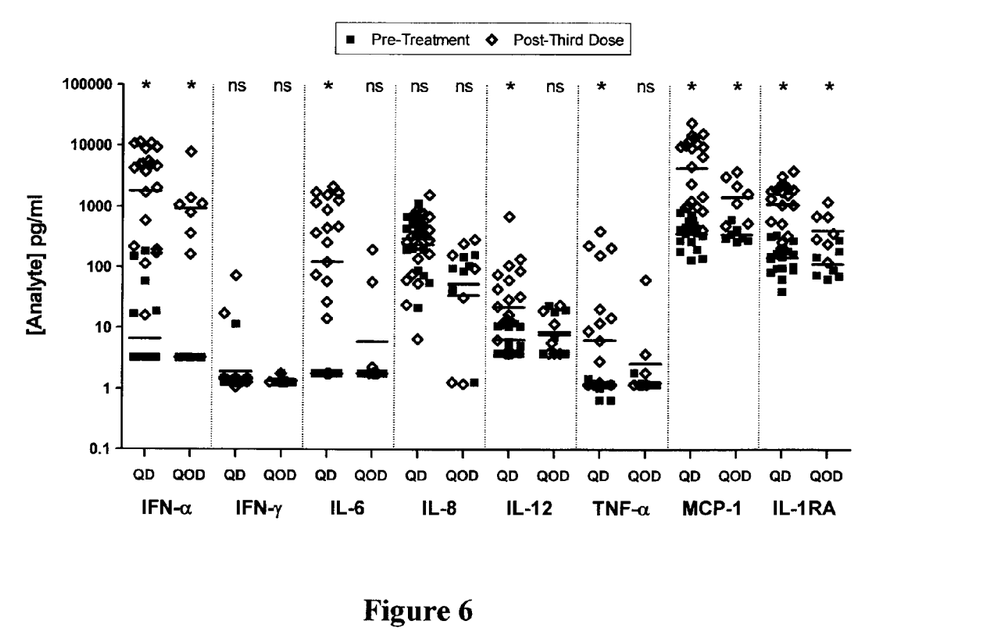
FIG. 6 shows induction of interferon-α and other cytokines following the 3rd dose of 100 mg/kg of Compound I as the tosylate on either the QD (D3) or QOD (D5) schedule. Pre-treatment values are also displayed. Each point indicates an individual animal. Fine lines indicate geometric mean. * indicates significant difference (p<0.05) between pre-treatment and post-dose values; ns: not significant. Non-responders are defined as animals with baseline interferon-α values after both the 1st and 2nd doses. Three such animals were excluded in the QOD group (n=7 final). No animals were excluded from the QD group (n=20 final).

While administration of the 3rd dose on a QD schedule induced higher levels of most cytokines than did administration on the QOD schedule (FIG. 6, Table 1), unexpectedly, the ratios of pro-inflammatory cytokines to IFN-α (after subtraction of pre-treatment values) were typically higher on the QD than the QOD schedule. Indeed, when expressed relative to IFN-α, the levels of IL-6, IL-12 and MCP-1 induced by the 3rd dose of compound I were all significantly higher (p<0.05) with QD compared to QOD dosing. This disparity equates to higher levels of pro-inflammatory cytokines relative to IFN-α after the 3rd dose administered on the QD compared to the QOD schedule. Notably, IL-6 and TNF-α were significantly induced (p<0.05) by the QD, but not by the QOD schedule. This highlights a qualitative difference in cytokine induction by the two schedules that likely contribute to differences in the type and durability of induced cellular responses (FIGS. 3-4). Since cytokines are key regulators of inflammation and the cellular immune response, these schedule dependent differences in relative cytokine induction may be reflected in corresponding differences in tolerability and/or efficacy.

In summary, these results indicate that modest, controlled cytokine and cellular responses sufficient for efficacy are induced by the alternate day schedule and that this pattern can be sustained over repeated dosing cycles. In addition, the QOD schedule is characterized by a greater level of IFN-α induction relative to most pro-inflammatory cytokines when compared to the QD schedule.

Example 2

Cyclic Dosing Schedule of 3 Days of Dosing Followed by 4 Days of Resting (3 On 4 Off)

Cynomolgus macaques were given either 30 mg/kg or 100 mg/kg of Compound I as the tosylate according to a dosing schedule of 3 consecutive days of dosing followed by 4 consecutive days of resting ('3 on 4 off') over 3 or 8 weeks. The immune response was determined by measuring cytokine and neopterin levels in plasma, as well as B cell and T cell responses in peripheral blood.

This schedule induced strong cytokine, chemokine, and neopterin responses that built with 3 repeated doses of Compound I Tosylate and declined during the non-dosing period from Days 4 to 7 as shown for IFN-α and neopterin in FIG. 1B. The cytokine and chemokine responses were reproducibly induced to a comparable magnitude with repeated courses of '3 on 4 off' dosing, which suggests that a 4-day-off-period is sufficient to re-set these responses between courses and implies that any counter regulation wanes in the intervening 4-day resting period. For example, IFN-α levels on the third day of individual cycles were 4192±768, 3832±1329 and 3879±1140 (average±SEM, n=4) when Compound I was administered at a dose of 100 mg/kg for three consecutive '3 on 4 off' cycles. T cell responses were elicited, which were either maintained or enhanced over repeated courses of '3 on 4 off' dosing (FIG. 3B). B cell proliferative state as measured by Ki67 levels was also enhanced with the response building upon each repeated course of treatment (FIG. 4B).

In summary, these results indicate that strong cytokine and cellular responses sufficient for efficacy were induced by the '3 on 4 off' schedule. Reproducible cycle-to-cycle immune activation without down-modulation of immune stimulation is observed.

Example 3

Schedule of Daily Dosing with No Rest Period (QD)

Cynomolgus macaques were given either 30 mg/kg or 100 mg/kg of Compound I as the tosylate or 2 mg/kg 852A for 7 consecutive days of QD dosing followed by 7 days of additional monitoring. The immune response was determined by measuring cytokine and neopterin levels in plasma, as well as B cell and T cell responses in peripheral blood.

Figure 5:
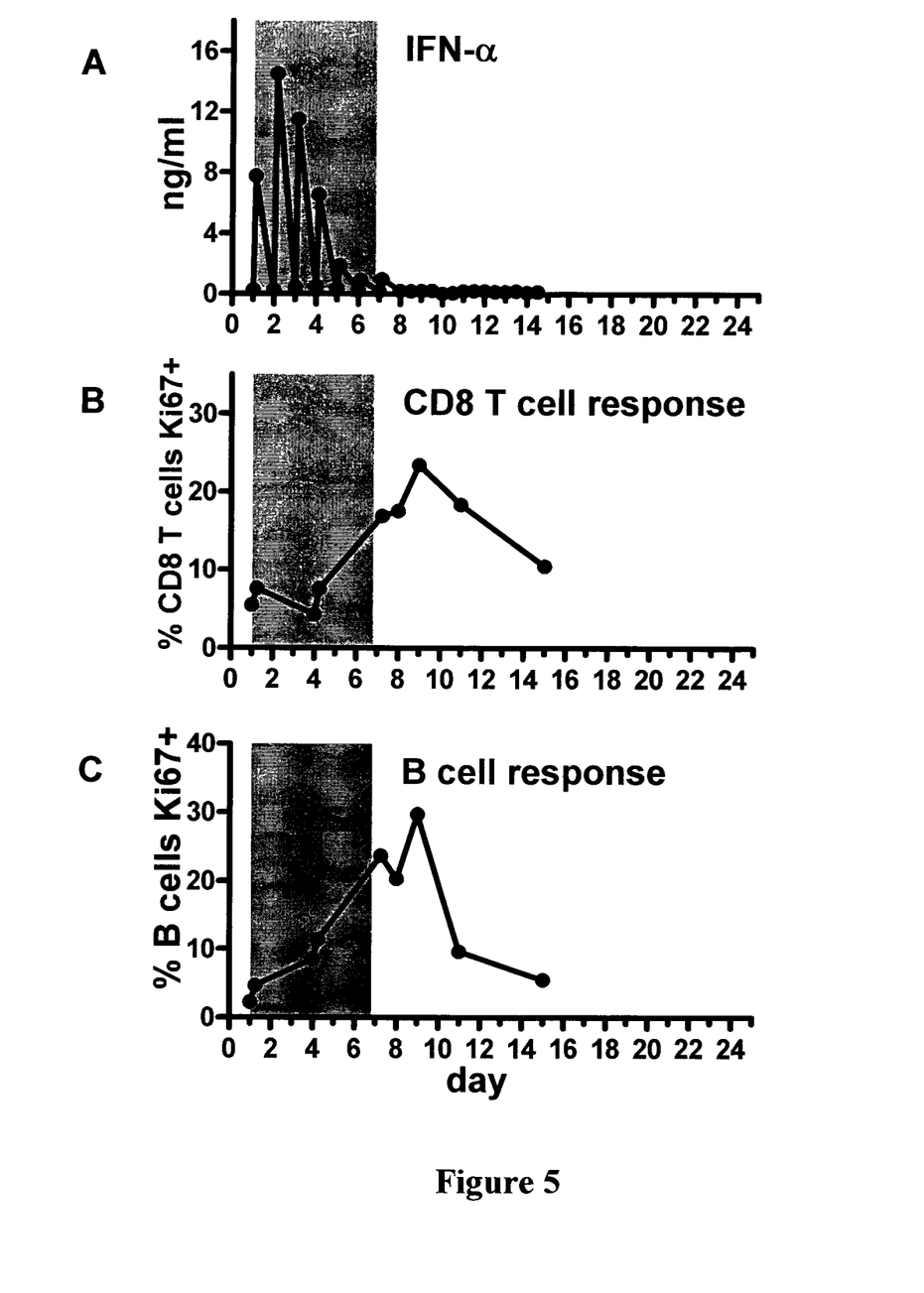
FIG. 5 shows interferon-α induction and cytotoxic T cell effector and B cell proliferative state for 2 mg/kg of N-[4-(4-amino-2-ethyl-1H-imidazo[4,5-c]quinolin-1yl)butyl-]methanesulfonamide ("Compound 852A"), an imidazoquinoline TLR7 agonist, according to a daily dosing (QD) schedule for 7 consecutive days with 7 days of follow-up. Compound 852A has previously been described by Dudek et al., CLIN CANCER RES., 13(23): 7119-25 (2007); Harrison et al., JOURNAL OF CLINICAL PHARMACOLOGY., 47:962-9 (2007). The gray backgrounds indicate dosing days.

This dosing schedule elicited strong cytokine and neopterin responses as shown for IFN-α and neopterin in FIGS. 1C and 5A. Surprisingly, levels of IFN-α and neopterin declined after peaking at 3-4 days of dosing with compound I tosylate (FIG. 1C) and day 2 of dosing with compound 852A (FIG. 5A). Unexpectedly, the decline in the initial IFN-α response was not dependent on the magnitude of response, since down-modulation is also triggered after administration of lower concentrations of compound I tosylate (FIG. 2). Despite this early down-modulation of cytokine levels, daily dosing elicited both B and T cell responses following the peak of cytokine production (FIGS. 3C, 4C, 5B, 5C) and B cell activation was induced throughout the dosing period. The magnitude of the B and T cell proliferative response was comparable to that elicited after 2-3 courses of the '3 on 4 off' schedule. The daily dosing schedule elicited a strong initial cytokine and neopterin response that was lost while drug was still being administered. As seen in FIGS. 1C, 2 and 5A, the cytokine and neopterin responses fall prior to the end of dosing, suggesting that counter regulatory mechanisms are induced to down-regulate the robust cytokine response.

Detailed analysis of the IFN-α data from cynomolgus monkeys studies described in Examples 1-3 are reported in Table 1. The IFN-α data demonstrates that there is repeatable induction to a comparable magnitude on dosing days with the QOD dosing schedule. In contrast, although there is significant induction of response at day 3 (p<0.05) with the QD dosing schedule, IFN-α levels are significantly reduced on day 5 (p<0.05) and day 7 (p<0.05) compared to day 3 for both Compound I tosylate and Compound 852A (shown below).

Compound 852A

Furthermore, the response on day 7 for the QD dosing schedule is markedly lower than the response on day 1 (10.3 fold lower for Compound 852A and 3.3 fold lower for the tosylate of Compound I). However, dosing according to a QOD dosing schedule shows responses that are roughly comparable throughout each cycle. Accordingly, the IFN-α level at day 7 for QOD dosing schedule is significantly higher than on day 7 for QD dosing schedule (15.8-fold for the tosylate of Compound I) (p<0.05). In addition to inducing a more controlled response compared to the QD dosing schedule, the QOD dosing schedule also induces a more moderate response than either the QD dosing schedule or '3 on 4 off' dosing schedule as shown by the levels of IFN-α at day 3.

The induction of response on the first few days of dosing and subsequent loss of response on subsequent days with the QD dosing schedule is comparable to the immune response induced by the first three dosing days of the '3 on 4 off' dosing schedule (FIGS. 1B and 1C), suggesting that similar beneficial immunostimulation can be induced over 7 days on the '3 on 4 off' schedule with fewer applied doses than the QD dosing schedule. However, dose 5 and subsequent doses with the '3 on 4 off' schedule appear to induce greater cytokine induction than equivalent doses with the QD schedule. For example, when IFN-α levels in plasma are compared after 6 doses of Compound I tosylate at 100 mg/kg (Compound I equivalents) administered according to either the QD dosing schedule (on Day 6) or the '3 on 4 off' dosing schedule (on day 3 in the second cycle), the level of this cytokine is markedly greater for the '3 on 4 off' dosing schedule (3832±1329) than for the QD dosing schedule (922±739) (p=0.057).

Taken together, this suggests that in general the '3 on 4 off' schedule can induce either a comparable or greater cytokine and chemokine response than the QD schedule, the relative magnitude being dependent on the number of administered doses.

TABLE 1

Mean Concentration of IFN-α Over Time
IFN-α (pg/ml)

| Day | QOD Compound I | 3 on 4 off Compound I | QD Compound I | QD Compound 852A |
|---|---|---|---|---|
| Pre-Treatment | Baseline | Baseline | Baseline | Baseline |
| Day 1 | 1293 ± 513 | 175 ± 69 | 498 ± 252 | 7496 ± 1880 |
| Day 3 | 1459 ± 634 | 4192 ± 768 | 8057 ± 1566 | 11235 ± 1362 |
| Day 5 | 1816 ± 1012 | Baseline* | 2166 ± 615 | 1625 ± 1137 |
| Day 7 | 2375 ± 982 | Baseline* | 151 ± 105 | 730 ± 205 |

Compound I was administered at 100 mg/kg per dose as the tosylate salt and Compound 852A at 2 mg/kg per dose. All values represent mean concentration of IFN-α ± SEM taken 3 hours after dosing at the indicated time points. Pre-treatment taken at pre-dose of Day 1 has been subtracted from subsequent values. Pre-treatment taken at pre-dose of Day 1 and * were taken at the same time that doses were administered on Days 1-3. Non-responders are defined as animals with baseline values on both the 1st and 2nd dose. 3 of 10 animals were excluded in the QOD group. No animals were excluded from the other groups.

The foregoing disclosure shows and describes only the preferred embodiments of the invention, but it is to be understood that the invention is capable of changes or modifications within the scope of the concept as expressed herein, commensurate with the above teachings and/or skill or knowledge of the relevant art. The embodiments described hereinabove are further intended to explain best modes known of practicing the invention and to enable others skilled in the art to utilize the invention in such, or other, embodiments and with the various modification required by the particular applications or uses disclosed herein. Accordingly, the description is not intended to limit the invention to the form disclosed herein. Also, it is intended that the appended claims be construed to include alternative embodiments.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

What is claimed:

1. A method of reducing down-modulation of cytokine or neopterin induction comprising administering a therapeutically effective amount of a optionally mono- or di-O-acetylated 3H-thiazolo[4,5-d]pyrimidin-2-one compound or a pharmaceutically acceptable salt thereof to a patient in need thereof according to a cyclical dosing schedule, wherein a cycle comprises a dosing period of at least one day in which a therapeutically effective amount of the optionally mono- or di-O-acetylated 3H-thiazolo[4,5-d]pyrimidin-2-one compound is administered, followed by a resting period of at least one day in which the optionally mono- or di-O-acetylated 3H-thiazolo[4,5-d]pyrimidin-2-one compound or pharmaceutically acceptable salt thereof is not administered, and wherein the optionally mono- or di-O-acetylated 3H-thiazolo[4,5-d]pyrimidin-2-one compound is or a pharmaceutically acceptable salt thereof.

2. The method of claim 1, wherein the dosing period is independently selected from 1, 2, 3, 4, and 5 days, and the resting period is independently selected from 1, 2, 3, 4, and 5 days.

3. The method of claim 1, wherein the dosing period is 1 day and the resting period is 1 day.

4. The method of claim 1, wherein the therapeutically effective amount of the optionally mono- or di-O-acetylated 3H-thiazolo[4,5-d]pyrimidin-2-one compound or pharmaceutically acceptable salt thereof is from about 0.1 mg/day to about 10,000 mg/day.

* * * * *